US00PP33438P2

(12) United States Plant Patent
Read et al.

(10) Patent No.: US PP33,438 P2
(45) Date of Patent: Aug. 31, 2021

(54) ***GAILLARDIA* PLANT NAMED 'FANFARE SHOWTIME'**

(50) Latin Name: ***Gaillardia* x *grandiflora***
Varietal Denomination: Fanfare Showtime

(71) Applicants: Charles Richard Read, Bognor Regis (GB); Jennifer Muriel Lintott, Bognor Regis (GB)

(72) Inventors: Charles Richard Read, Bognor Regis (GB); Keith George Lintott, Bognor Regis (GB)

( * ) Notice: Subject to any disclaimer, the term of this patent is extended or adjusted under 35 U.S.C. 154(b) by 0 days.

(21) Appl. No.: 17/071,533

(22) Filed: Oct. 15, 2020

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
CPC ..... A01H 6/14
See application file for complete search history.

*Primary Examiner* — Anne Marie Grunberg
(74) *Attorney, Agent, or Firm* — Weatherly IP Solutions, LLC; Barbara Campbell

(57) ABSTRACT

A new variety of *Gaillardia* plant named 'Fanfare Showtime' that is distinguishable by a compact and upright plant habit, large inflorescences composed of bicolored cream-yellow and pink-red tubular ray flowers arranged around a central disc, is disclosed.

2 Drawing Sheets

Genus and species: *Gaillardia* x *grandiflora*.
Variety denomination: 'Fanfare Showtime'.

BACKGROUND OF THE NEW PLANT

The present invention relates to a new and distinct variety of *Gaillardia*, commonly known as blanket flower, an herbaceous perennial that is grown for use as an ornamental landscape and container plant. The new plant is known botanically as *Gaillardia* x *grandiflora* and will be referred to hereinafter by the variety name 'Fanfare Showtime'. *Gaillardia* is in the family Compositae, under which the commonly referred to "flower" is actually the inflorescence, and made up of showy ray flowers and small disc florets.

'Fanfare Showtime' is the result of a controlled hybridization carried out in 2014 in West Sussex, England. The male and female parents were selected from previously hybridized selections which are unreleased and unpatented. The female parent of 'Fanfare Showtime' is *Gaillardia* seedling 'G1316-5' and the male parent of 'Fanfare Showtime' is *Gaillardia* seedling 'G1317-2'.

'Fanfare Showtime' was first asexually reproduced in 2015 by rooting softwood cuttings in a greenhouse at a nursery in West Sussex, United Kingdom. Since that time, 'Fanfare Showtime' has been determined to be stable and remains true-to-type in successive generations of asexual reproduction via softwood cuttings.

SUMMARY

The following traits have been repeatedly observed and represent the distinguishing characteristics of 'Fanfare Showtime'. 'Fanfare Showtime' has not been tested under all possible conditions and phenotypic differences may be observed with variations in environmental, climatic, and cultural conditions, without any variance in genotype.

1. 'Fanfare Showtime' exhibits a compact and upright plant habit.
2. 'Fanfare Showtime' bears large showy inflorescences composed of tubular ray flowers arranged around a central disc composed of numerous small disc florets.
3. When fully expanded, the tubular ray flowers of 'Fanfare Showtime' are bi-colored, consisting of pink-red coloration of the corolla tube and cream-yellow coloration to the petal apices.
4. 'Fanfare Showtime' is 30 cm to 35 cm in height and 35 cm to 40 cm in width after one year's growth from a rooted cutting.
5. 'Fanfare Showtime' is hardy at least to USDA Zone 6.

BRIEF DESCRIPTION OF THE PHOTOGRAPHS

The accompanying color photographs illustrate the overall appearance of the new *Gaillardia* cultivar 'Fanfare Showtime' showing the colors as true as is reasonably possible to obtain in colored reproductions of this type. Colors in the photograph may differ from the color values cited in the detailed botanical description, which more accurately describes the actual colors of the new variety 'Fanfare Showtime'.

Figure 1:
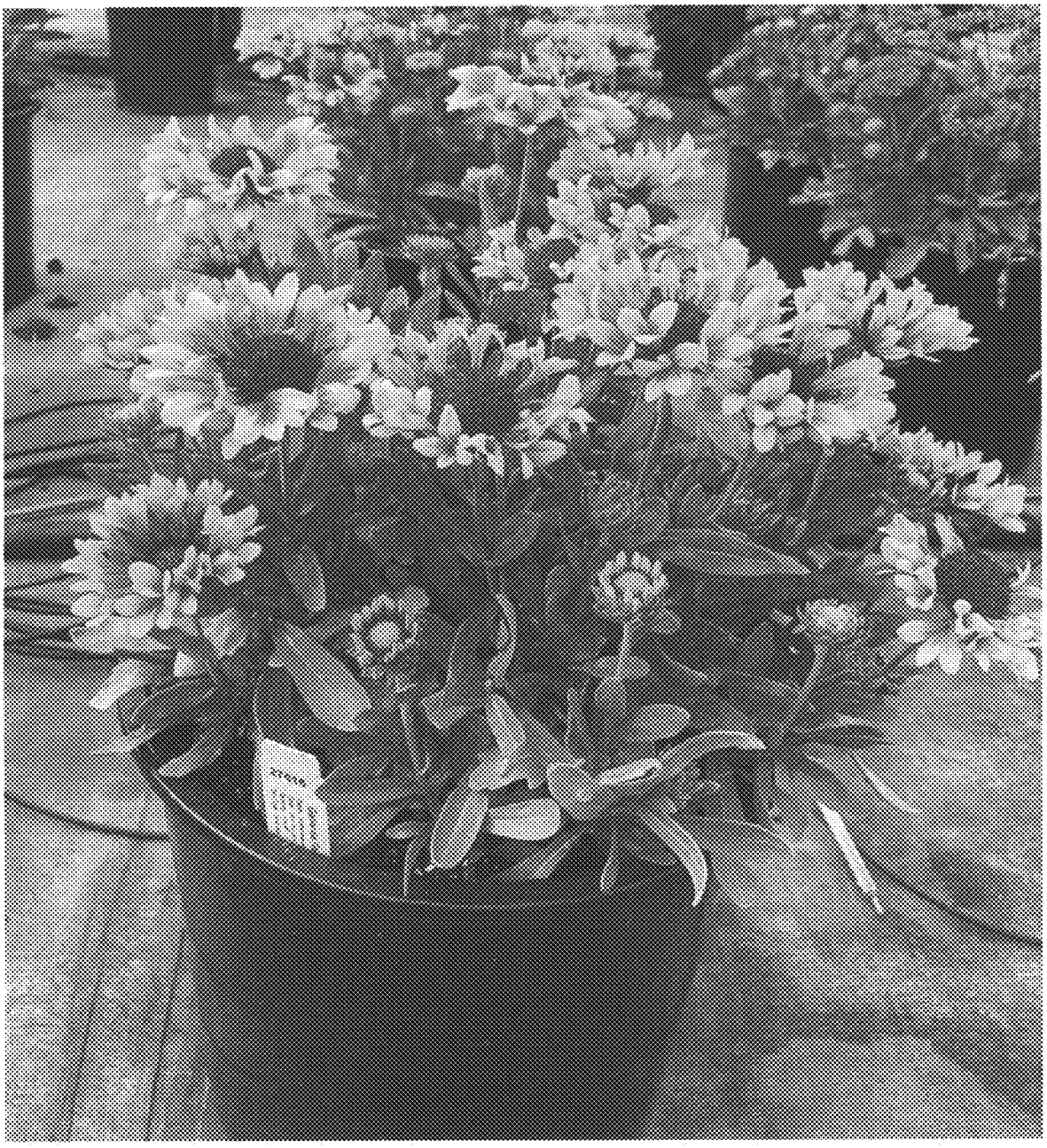

FIG. 1 depicts a whole plant of 'Fanfare Showtime' growing outdoors in Oxnard, Calif. The plant is one-year-old from a cutting. The photograph was taken in the first week of June 2020 when the variety was first coming into full-bloom.

Figure 2:
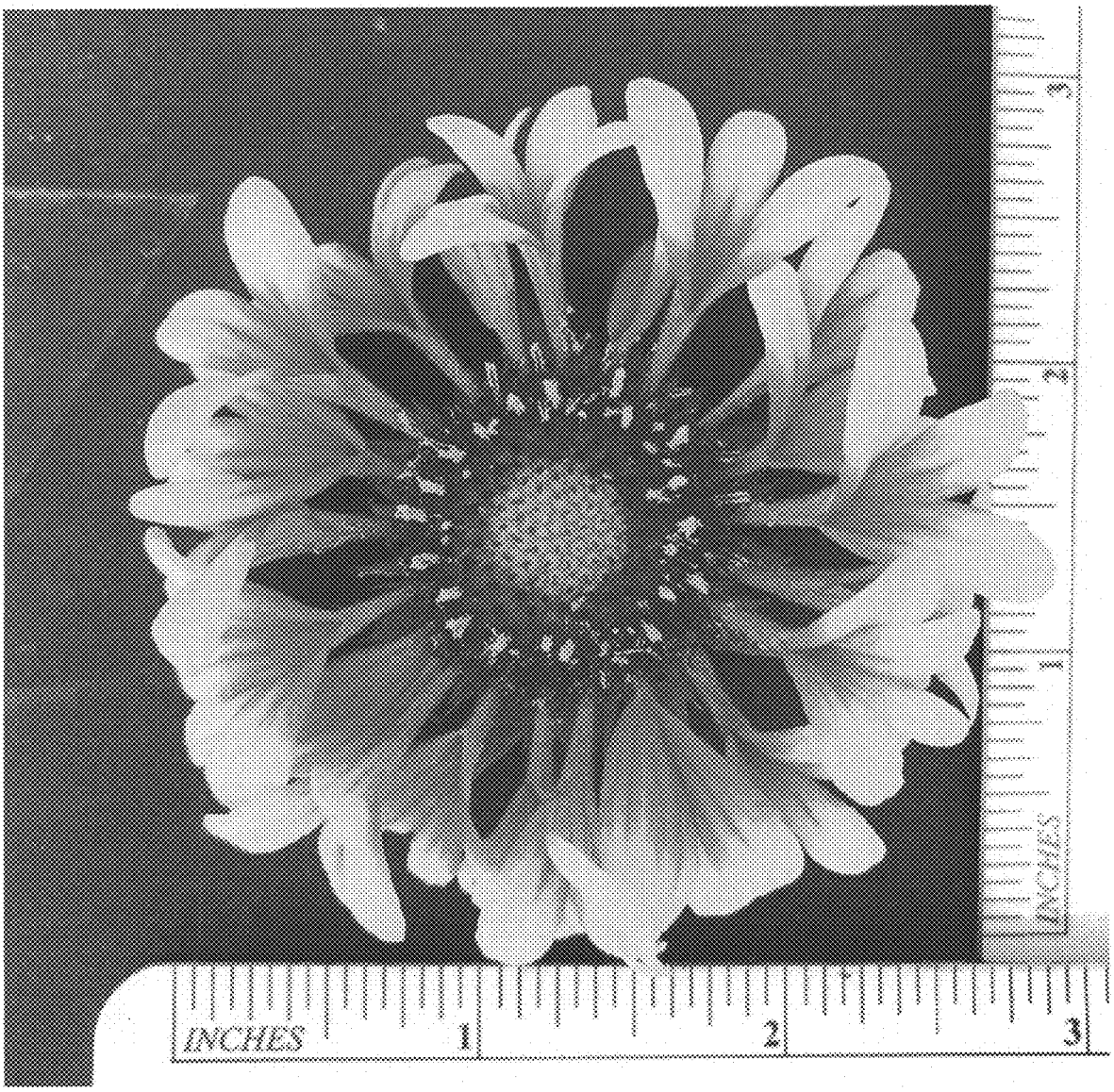

FIG. 2 depicts a fully-expanded inflorescence of 'Fanfare Showtime'.

BOTANICAL DESCRIPTION OF THE PLANT

The following is a detailed botanical description of the new *Gaillardia* x *grandiflora* variety 'Fanfare Showtime'. Observations, measurements, values and comparisons were compiled in Santa Barbara, Calif. from a one-year-old plant growing in a 2-gallon container. The plant had been grown in an unheated greenhouse during the rooting stage and transferred to an open-air bed until flowering. Color determinations are made by reference to the 2007 edition of The Royal Horticultural Society Colour Chart from London, England, except where general color terms of ordinary significance are used.

Botanical classification:

*Genus.*—*Gaillardia.*

*Species.*—x *grandiflora.*

*Common name.*—Blanket flower.

Parentage:

*Gaillardia* x *grandiflora 'Fanfare Showtime' was selected as seedling which resulted from the controlled cross of the following parent plants.*—Female parent: Proprietary *Gaillardia* seedling 'G1316-5'. Male parent: Proprietary *Gaillardia* seedling 'G1317-2'.

Plant:

*Propagation method.*—Softwood cuttings.

*Rooting system.*—Fine and fibrous.

*Vigor.*—Moderate vigor.

*Time to develop roots.*—14 to 20 days are needed for an initial cutting to develop roots.

*Temperature to develop roots.*—The recommended air temperature is 20 to 21° Centigrade.

*Crop time.*—Approximately 12 weeks to first flowering from planting a rooted cutting.

*Growth habit.*—Compact, low growing and upright.

*Branching habit.*—Lateral branching is encouraged by pinching or stopping the stem at 5 cm to 8 cm above the growing surface.

*Suggested container size.*—1-gallon container.

*Use.*—Ornamental for use as a landscape plant or container plant.

*Type.*—Herbaceous perennial.

*Height of plant.*—30 cm to 35 cm.

*Width of plant.*—35 cm to 40 cm.

*Cultural requirements.*—Grow in full sun with moderate water, avoiding drying out or saturation.

*Resistance or susceptibility to diseases and pests.*—In common with all plants of the genus, 'Fanfare Showtime' is susceptible to bacterial pathogens associated with overwatering, and to feeding by thrips *Thysanoptera*) and aphids (*Aphididae*).

*Hardiness.*—Survives in USDA Hardiness Zone 6 (not tested in colder zones).

*Flowering period.*—Flowering will commence typically in May or June according to the region and season and will continue until September or October.

Stem, branches:

*Stem dimensions.*—5 cm to 8 cm in length if pinched or stopped at that height, 5 mm in diameter at the base.

*Stem color.*—145B.

*Stem shape.*—Round.

*Stem surface.*—Villous, hairs fine, 2 mm in length, color NN155C.

*Branches.*—3 to 5 lateral branches if main stem is pinched or stopped at 5 cm to 8 cm in height.

*Lateral branch dimensions.*—15 cm to 20 cm in length, 3 mm to 4 mm in diameter.

*Lateral branch color, shape, surface.*—RHS 145B.

Foliage:

*Type.*—Evergreen.

*Leaf arrangement.*—Alternate.

*Leaf form.*—Simple.

*Margin.*—Entire.

*Leaf shape.*—Oblanceolate.

*Leaf length.*—10 cm in length.

*Leaf width.*—1.5 cm to 2.0 cm in width.

*Leaf base.*—Attenuate.

*Leaf apex.*—Rounded.

*Leaf venation pattern.*—Pinnate.

*Midrib vein.*—Prominent, broad, up to 2 mm in width towards base, raised 0.5 mm on abaxial surface.

*Vein color* (*both surfaces*).—193C.

*Leaf surface* (*both surfaces*).—Pubescent.

*Leaf surface* (*adaxial surface*).—Pubescent, hairs very short and fine, color NN155C.

*Leaf attachment.*—Sessile.

*Leaf color* (*both surfaces*).—138A.

*Fragrance.*—Sage-like scent, strong when rubbed.

Inflorescence:

*Inflorescence.*—Solitary.

*Aspect.*—Facing upward.

*Dimensions of inflorescence.*—75 mm in diameter and 20 mm in depth.

*Inflorescence type.*—Radiate capitate.

*Inflorescence shape.*—Radiate with center disc.

*Number of inflorescences per plant.*—Approximately 30 inflorescences in colored bud and flower at one time.

*Blooming season.*—Spring, summer and fall.

*Peduncle dimensions* (*above uppermost leaf*).—Length varies between 2 cm and 10 cm, diameter 2.5 mm to 3.0 mm.

*Peduncle shape.*—Cylindrical.

*Peduncle surface.*—Surface is pubescent and exhibits longitudinal parallel ridges 0.5 mm apart.

*Peduncle color.*—Ridges 145B alternating with 138A between ridges.

*Peduncle strength.*—Very stiff.

Bud:

*Shape.*—Rotate whorl.

*Dimensions* (*immediately prior to cracking color*).—12 mm in diameter, 10 mm in depth.

*Color.*—138B.

Ray flowers:

*Ray flower shape.*—Tubular.

*Ray flower surface* (*both surfaces*).—Smooth, glabrous.

*Ray flower arrangement.*—Radiate.

*Number of ray flowers per inflorescence.*—20 to 25.

*Number of petals per ray flower.*—Four.

*Fused or unfused.*—Petals are partially longitudinally fused to form corolla tube.

*Petal margins of ray flowers.*—Entire.

*Ray flower dimensions* (*overall, from base of corolla tube to petal apices*).—28 mm in length, up to 25 mm in width measured across petal apices.

*Corolla tube dimensions* (*petals fully fused*).—9 mm in length, 2 mm in diameter at tube base.

*Corolla tube color* (*both surfaces*).—52A.

*Color of ray flower petals* (*both surfaces*).—52A with longitudinal stripes 47B.

*Color of ray flower petal flared apices.*—Initially 52A with stripes 47B becoming entirely cream-yellow 13B to 13C towards and at petal apex.

*Self-cleaning or persistent.*—Self-cleaning.

Disc florets:

*Quantity of disc florets per inflorescence.*—Approximately 80 disc florets per inflorescence.

*Disc dimensions.*—25 mm.

*Disc floret dimensions.*—10 mm. in length and 3 mm in diameter.

*Disc floret corolla tube.*—6 mm in length.

*Surface of disc florets.*—Lanate.

*Disc floret color.*—187C.

*Chaff* (*surrounds disc floret corolla tube*).—Translucent, paper-like, 6 mm in length, bearing 3 or 4 hair-like spurs, 3 mm to 4 mm in length.

*Chaff color, including spurs.*—155A.

*Phyllary dimensions.*—3 cm. in diameter and 1 cm. in height.

*Phyllary color.*—147B.

*Phyllary arrangement.*—Whorl.

*Number of involucral bracts.*—An average of 25 in number per inflorescence.

*Shape of involucral bract.*—Oblanceolate.

*Involucral bract arrangement.*—2 to 3 layered whorls, typically 8 large bracts in lowest whorl, and approximately 14 smaller bracts in upper whorls.

*Involucral bract dimensions* (*lowest whorl*).—14 mm in length, 6 mm in width.

*Involucral bract dimensions* (*upper whorls*).—10 mm in length, 3.5 mm in width.

*Involucral bract margin.*—Entire.

*Involucral bract apex.*—Acute.

*Involucral bract base.*—Truncate.

*Involucral bract color* (*both surfaces*).—143B.

*Involucral bract surface* (*both surfaces*).—Pubescent.

*Involucral bract surface* (*adaxial surface*).—Lightly pubescent, hairs 1 mm to 2 mm in length, color NN155C.

*Fragrance of inflorescence.*—Very slight only when closely observed.

Reproductive organs:

*Number of stamens.*—3 to 5.

*Stamen dimensions.*—2 mm to 3 mm. in length, less than 0.5 mm in diameter.

*Stamen color.*—21B.

*Stamen form.*—Plumose.

*Anthers.*—Ellipsoidal, 0.50 mm in length and less than 0.5 mm in width.

*Anther color.*—166B.

*Pollen.*—Present, copious amount.

*Pollen color.*—9A.

*Pistil.*—1, strongly exserted, 12 mm in length, less than 0.5 mm in diameter.

*Stigma.*—8 mm in length, upper 4 mm bifurcated, reflexed.

*Stigma color.*—166B.

*Ovary.*—Position inferior, shape globose, observed immature, diameter 1.5 mm, color 157D.

*Seed.*—No seed has been observed.

COMPARISON WITH PARENTAL LINES AND KNOWN VARIETY

'Fanfare Showtime' exhibits the following characteristics of the male and female parents. The male parent 'G1317-2' bears cream and light-pink colored fluted petals. The female parent 'G1316-5' bears cream and copper-colored fluted petals and has a compact plant habit. In comparison with the male parent, 'Fanfare Showtime' has a more compact habit, darker pink coloration to the fluted petals and a larger inflorescence. In comparison with the female parent, 'Fanfare Showtime' is more vigorous and bears pink-red rather than copper colored fluted petals.

The most similar variety of *Gaillardia* relative to 'Fanfare Showtime' is *Gaillardia* 'Fanfare' (U.S. Plant Pat. No. 15,892). Both 'Fanfare' and 'Fanfare Showtime' bear bicolored tubular ray flowers. The flowers of 'Fanfare Showtime' are cream and pink-red in color when fully expanded, whereas the flowers of 'Fanfare' are yellow-orange and bright red in color at all stages. 'Fanfare Showtime' presents a softer and more muted appearance in the garden and landscape. In addition, whereas 'Fanfare' grows with a slightly spreading plant habit, the plant habit of 'Fanfare Showtime' is upright and shorter in overall height.

We claim:

1. A new and distinct cultivar of *Gaillardia* x *grandiflora* plant named 'Fanfare Showtime' as described and illustrated.

* * * * *